(12) United States Patent
Schwab

(10) Patent No.: US 8,372,146 B2
(45) Date of Patent: Feb. 12, 2013

(54) DISTENSIBLE LIGAMENT SYSTEMS

(75) Inventor: Frank J. Schwab, New York, NY (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 260 days.

(21) Appl. No.: 12/412,004

(22) Filed: Mar. 26, 2009

(65) Prior Publication Data

US 2010/0249928 A1   Sep. 30, 2010

(51) Int. Cl.
*A61F 2/08*   (2006.01)
(52) U.S. Cl. ........... 623/13.14; 623/13.11; 623/13.13
(58) Field of Classification Search ............ 606/103, 606/251, 252, 258; 623/13.11, 13.14, 13.13
See application file for complete search history.

(56) References Cited

U.S. PATENT DOCUMENTS

| | | | |
|---|---|---|---|
| 5,672,175 A | 9/1997 | Martin | |
| 6,613,050 B1 | 9/2003 | Wagner et al. | |
| 6,989,011 B2 | 1/2006 | Paul et al. | |
| 7,083,622 B2 * | 8/2006 | Simonson | 606/279 |
| 7,137,985 B2 | 11/2006 | Jahng | |
| 7,229,441 B2 | 6/2007 | Trieu et al. | |
| 7,377,921 B2 | 5/2008 | Studer et al. | |
| 7,438,715 B2 | 10/2008 | doubler et al. | |
| 2009/0093820 A1 * | 4/2009 | Trieu et al. | 606/103 |

* cited by examiner

*Primary Examiner* — Thomas J Sweet
*Assistant Examiner* — Matthew Schall

(57) ABSTRACT

Distensible ligaments and distensible ligament systems are provided, including apparatuses, systems, devices, hardware, methods, and combinations for distensible systems.

7 Claims, 3 Drawing Sheets

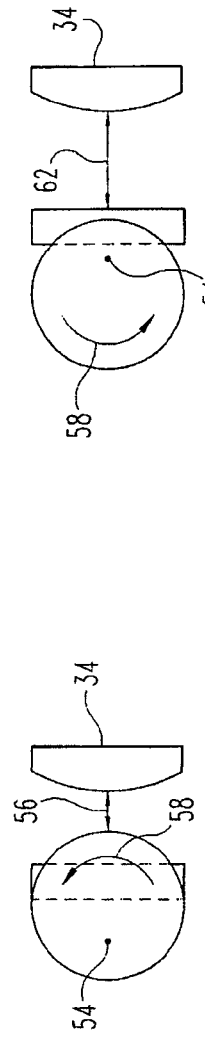
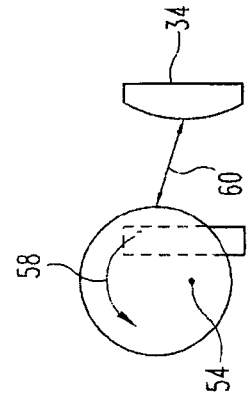
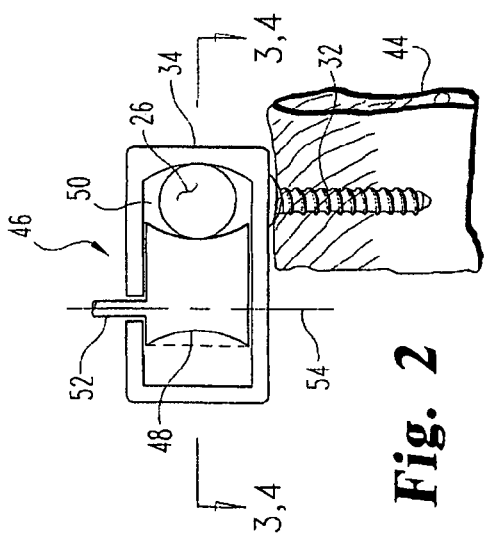
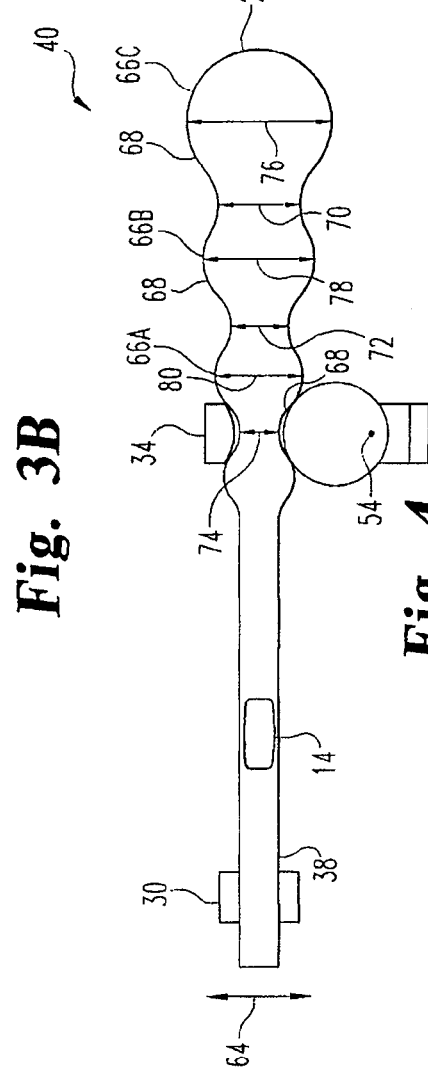

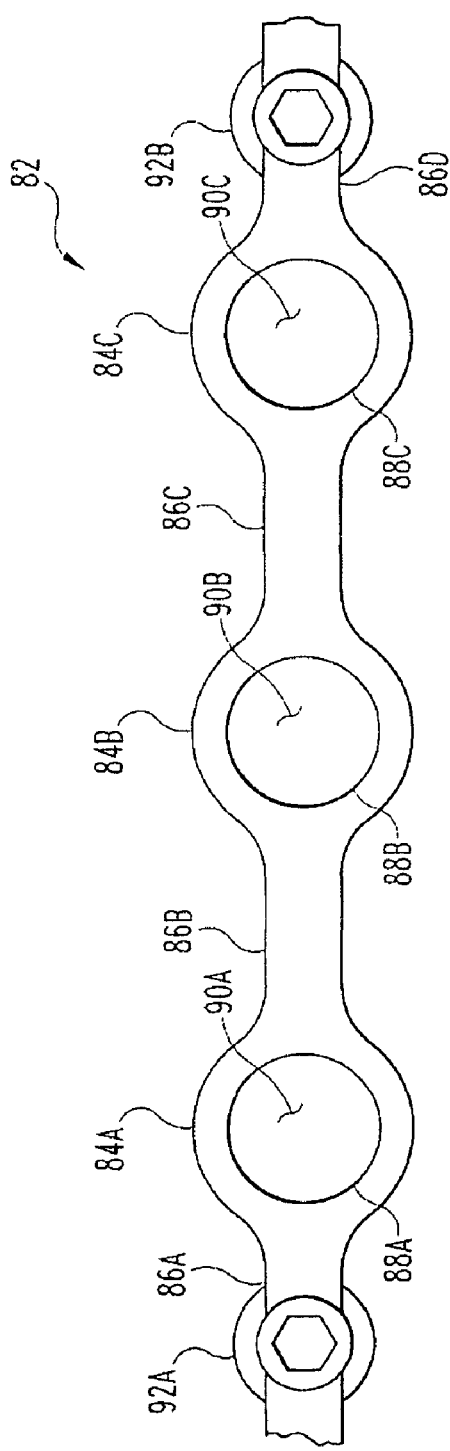
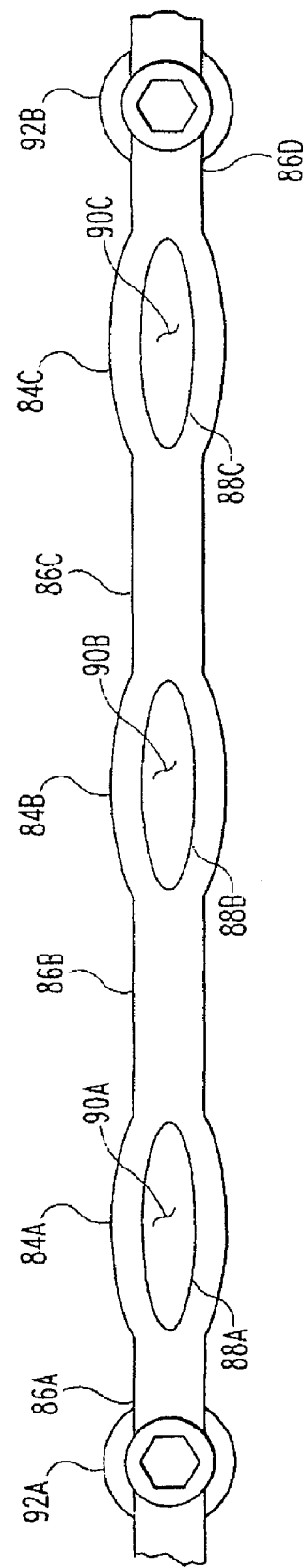
Fig. 5A
Fig. 5B

DISTENSIBLE LIGAMENT SYSTEMS

FIELD OF THE INVENTION

The present invention relates to devices and methods for use in spinal repair, and more particularly, to devices, systems and methods for stabilizing the spine.

BACKGROUND

Corrective and other surgeries of the human body often require the implantation of ligaments, for example, to replace or augment existing ligaments or effect changes in position or alignment between bone structures, e.g., intervertebral spinal ligaments. Current implants have a limited elasticity/elongation, which may not be optimal. Accordingly, there is a need for improved ligament systems.

SUMMARY

One embodiment of the present invention includes a unique distensible ligament system. Another embodiment of the present invention is a unique distensible ligament. Other embodiments include apparatuses, systems, devices, hardware, methods, and combinations for distensible ligament systems. Further embodiments, forms, features, aspects, benefits, and advantages shall become apparent from the description and figures provided herewith.

BRIEF DESCRIPTION OF THE DRAWINGS

The description herein makes reference to the accompanying drawings wherein like reference numerals refer to like parts throughout the several views, and wherein:

FIG. 2 graphically illustrates a distensible ligament system in accordance with an embodiment of the present invention.

FIGS. 3A-3C depict a gate of a variable receiver of an embodiment of the present invention in three different positions.

FIG. 4 illustrates a ligament and variable receiver in accordance with an embodiment of the present invention.

FIGS. 5A and 5B depict a cross sectional view of a distensible ligament in accordance with an embodiment of the present invention.

DETAILED DESCRIPTION

Figure 1:
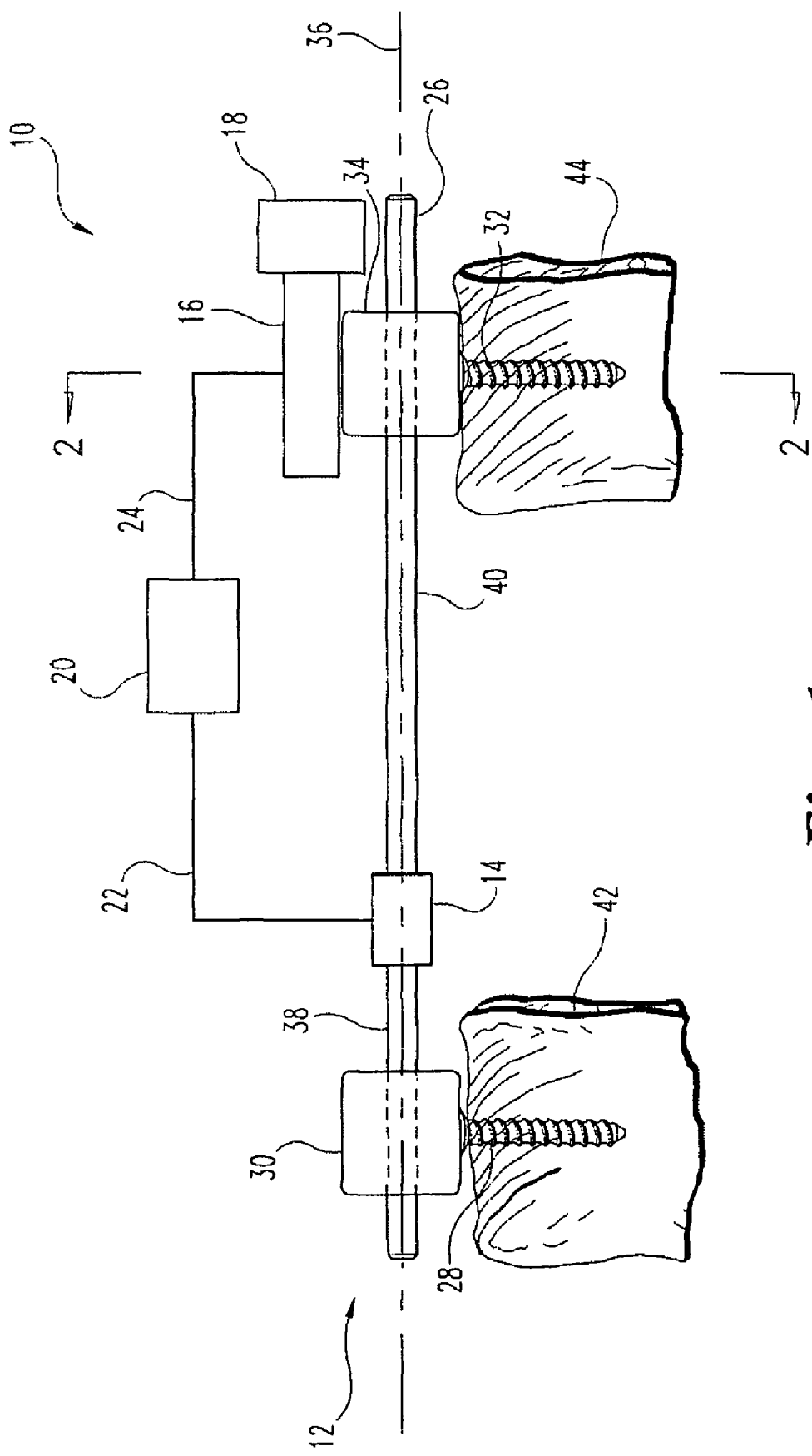
FIG. 1 schematically illustrates a system for controlling tension in a ligament, in particular, in a distensible ligament system, in accordance with an embodiment of the present invention.

For purposes of promoting an understanding of the principles of the invention, reference will now be made to the embodiments illustrated in the drawings, and specific language will be used to describe the same. It will nonetheless be understood that no limitation of the scope of the invention is intended by the illustration and description of certain embodiments of the invention. In addition, any alterations and/or modifications of the illustrated and/or described embodiment(s) are contemplated as being within the scope of the present invention. Further, any other applications of the principles of the invention, as illustrated and/or described herein, as would normally occur to one skilled in the art to which the invention pertains, are contemplated as being within the scope of the present invention.

Referring now to the drawings, and in particular, FIG. 1, a system 10 for controlling tension in a ligament is schematically depicted. System 10 includes a distensible ligament system 12, a sensor 14, a drive unit 16 with a power supply 18, and a controller 20. Controller 20 is communicatively coupled to sensor 14 via a communications link 22. Controller 20 is communicatively coupled to drive unit 18 via a communications link 24.

Distensible ligament system 12 is implanted into a living patient, e.g., a human patient, and includes a ligament 26, an anchor 28 having a receiver 30, and an anchor 32 having a variable receiver 34. Ligament 26 is defined by a major axis 36 extending along the length of ligament 26. Ligament 26 may be symmetric about major axis 36. Ligament 26 includes a first lengthwise extent, e.g., a span 38, and a second lengthwise extent, e.g., a span 40. As described herein, span 40 may have different physical characteristics than span 38.

It is contemplated that ligament 26 may be flexible, tear resistant, and/or suturable. Ligament 26 may be fabricated from synthetic flexible materials in the form of fabrics, nonwoven structures, two or three dimensional woven structures, braided structures, and chained structures. Ligament 26 may also be fabricated from natural/biological materials, such as autograft or allograft, taken from patellar bone-tendon-bone, hamstring tendons, quadriceps tendons, or Achilles tendons, for example. Growth factors or cells can be incorporated into ligament 26 for bone ingrowth and bony attachment or for soft tissue ingrowth. Possible growth factors that can be incorporated include transforming growth factor β1, insulin-like growth factor 1, platelet-derived growth factor, fibroblast growth factor, bone morphogenetic protein, LIM mineralization protein (LMP), and combinations thereof.

Possible ligament 26 materials include synthetic resorbable materials such as polylactide, polyglycolide, tyrosine-derived polycarbonate, polyanhydride, polyorthoester, polyphosphazene, calcium phosphate, hydroxyapatite, bioactive glass and combinations thereof. Possible ligament 26 materials also include natural resorbable materials such as autograft, allograft, xenograft, soft tissues, connective tissues, demineralized bone matrix, and combinations thereof. Possible ligament 26 materials further include nonresorbable materials such as polyethylene, polyester, polyvinyl alcohol, polyacrylonitrile, polyamide, polytetrafluorethylene, polyparaphenylene terephthalamide, cellulose, shape-memory alloys, titanium, titanium alloys, stainless steel, and combinations thereof.

Anchor 28 is structured for anchoring into a bone tissue location 42, e.g., a pedicle of a spinal vertebra. Receiver 30 is structured to secure span 38 of ligament 26 to anchor 28. Anchor 32 is structured for anchoring into a bone tissue location 44, e.g., a pedicle of a spinal vertebra. Variable receiver 34 is structured to secure span 40 to anchor 32. It should be understand that systems are contemplated that include more than two anchors, and anchors engaged to more than two vertebrae or other bone structures, such as the pelvis.

In addition, variable receiver 34 is structured to perform an in vivo release of at least a portion of span 40 of ligament 26, thus extending the length of ligament 26 as between anchors 28 and 32. That is, variable receiver 34 is structured to release at least a portion of span 40 to relieve tension in ligament 26 subsequent to implantation into the patient, e.g., after completion the implantation surgery and closure of the surgical site. This may allow, for example, implantation of ligament 26 during a surgical procedure, after the completion of which the patient may be free to go home; distension of ligament 26 may then be performed without a further surgical procedure.

It is contemplated that anchors 28 and 32 may be, for example, interference screws or anchors, gull anchors, suture anchors, pin fasteners, bone screws with spiked washers, staples, and buttons. In addition, it is contemplated that the anchors may be made from resorbable materials, nonresorbable materials, and combinations thereof. Possible synthetic resorbable materials include polylactide, polyglycolide, tyrosine-derived polycarbonate, polyanhydride, polyorthoester, polyphosphazene, calcium phosphate, hydroxyapatite, bioactive glass, and combinations thereof. Possible natural resorbable materials include cortical bone, autograft, allograft, and xenograft. Possible nonresorbable materials include carbon-reinforced polymer composites, shape-memory alloys, titanium, titanium alloys, cobalt chrome alloys, stainless steel, and combinations thereof.

Sensor 14 is coupled to ligament 26, and is structured to provide a tension signal indicative of the tension in ligament 26. Sensor 14 may include, for example, a strain gage. In the present embodiment, sensor 14 is positioned inside ligament 26. In other embodiments, it is alternatively contemplated that sensor 14 may be located external to ligament 26, e.g., mounted on an external surface of ligament 26, or mounted on anchor 28, receiver 30, anchor 32 or receiver 34, in which case, for example, the tension in ligament 26 may be sensed indirectly.

Drive unit 16 is coupled to variable receiver 34. Drive unit 16 is structured to receive a control signal, and in response thereto, to drive variable receiver 34 from a one position to another position, e.g., as described herein, to perform the in vivo release of ligament 26. Drive unit 16 may be, for example, a geared motor, a linear actuator, or any electromechanical drive capable of providing motive force to drive variable receiver 34 into the desired position.

Power supply 18 is a battery. It is alternatively contemplated that in other embodiments, other types of power sources may be employed, such as a subdermally implanted induction coil.

Controller 20 is configured to execute program instructions to generate a control signal in response to a tension signal from sensor 14 that is indicative of tension in ligament 26, and to provide the control signal to drive unit 16. Controller 20 may be, for example, similar to the controller of a pacemaker, an implantable pump, or an external pump.

In the present embodiment, controller 20 is microprocessor based, and the program instructions are in the form of software stored in a memory (not shown). However, it is alternatively contemplated that the controller and program instructions may be in the form of any combination of software, firmware and hardware, including state machines, and may reflect the output of discreet devices and/or integrated circuits, which may be co-located at a particular location or distributed across more than one location, including any digital and/or analog devices configured to achieve the same or similar results as a processor-based controller executing software or firmware based instructions.

Communications link 22 may be a digital and/or analog communications link, and may be a wired communication link, a wireless connection, an optical cable link or any system capable of transmitting a signal from sensor 14 to controller 20. Similarly, communications link 24 may be a digital and/or analog communications link, and may be a wired communication link, a wireless connection, an optical cable link or any system capable of transmitting a signal from controller 20 to drive unit 18. In addition, communications link 24 may be a unidirectional communications link, or may be a bidirectional communications link capable of transmitting information from drive unit 18 to controller 20, e.g., feedback information indicative of the position of variable receiver 34.

Referring now to FIG. 2, aspects of distensible ligament system 12, in particular, variable receiver 34, are further described. Receiver 34 is a variable latch that is structured to move between a plurality of positions, e.g., to move between one position and another position to perform the in vivo release of ligament 26. The plurality of positions may be a continuum, e.g., extending continuously between two extreme positions. In the present embodiment, receiver 34 in the form of a gate 46 having an eccentric 48 and variable opening 50. Variable opening 50 extends in a direction transverse to the major dimension of ligament 26, i.e., transverse to major axis 36. Gate 46 is structured to increase the size of variable opening 50 in the transverse direction. It will be understood that other mechanisms that provide a variable opening may be used in other embodiments of the present invention.

Eccentric 48 includes a drive shaft 52 that is turned by drive unit 16 in order to rotate eccentric 48 about an axis of rotation 54. In one form, axis of rotation 54 is substantially perpendicular to an axis through the major dimension of ligament 26, i.e., major axis 36, although other embodiments may employ different orientations of axis of rotation 54. The rotation of eccentric 48 about axis of rotation 54 increases or decreases the size of variable opening 50, depending upon the direction of rotation.

For example, referring now to FIGS. 3A-3C, receiver 34 is illustrated with eccentric 48 in three different positions. FIGS. 3A-3C are cross sectional views of the depiction of FIG. 2. It will be understood that eccentric 48 is rotatable into other positions not illustrated herein. FIG. 3A illustrates gate 46 with eccentric 48 in a first position having a size 56 of variable opening 50 transverse to major axis 36. A rotation of eccentric 48, e.g., in direction 58, results in a larger size 60 of variable opening 50, e.g., as illustrated in FIG. 3B. A further rotation of eccentric 48 results in a still larger size 62 of variable opening 50, e.g., as depicted in FIG. 3C.

Referring now to FIG. 4, aspects of distensible ligament system 12 are yet further described. FIG. 4 is a cross sectional plan view of the depiction of FIG. 2, and illustrates one embodiment of ligament 26 and variable receiver 34.

In the embodiment of FIG. 4, span 40 of ligament 26 increases in ligament transverse dimension, e.g., direction 64 that is transverse to major axis 36 of ligament 26. As depicted in the present Figures, span 40 of ligament 26 has a generally circular cross section. However, it will be understood that other cross sections may be employed, such as a relatively flat cross section that has a major dimension in transverse direction 64. Span 40 increases in transverse dimension with increasing distance from span 38, i.e., in the direction extending from receiver 30 to variable receiver 34. In the present embodiment, span 40 includes a plurality of nodes 66 and a corresponding plurality of segments 68. In the depicted embodiment, three (3) nodes 66 are depicted—nodes 66A, 66B and 66C.

Segments 68 may increase in transverse dimension with increasing distance from span 38. For example, transverse dimension 70 of ligament 26 is greater than transverse dimension 72, which is greater than transverse dimension 74. Similarly, nodes 66 may successively increase in transverse dimension with increasing distance from span 38. For example, transverse dimension 76 is greater than transverse dimension 78, which is greater than transverse dimension 80.

By increasing in transverse dimension with increasing distance from span 38, a ramped wedge-like structure is obtained. Although nodes 66 with segments 68 are employed in the present embodiment to yield a wedge structure, it will be understood that other geometries may be employed in other embodiments of the present invention. For example, in one elemental form, span 40 may be a single segment that increases in transverse dimension, e.g., linearly nor nonlinearly, with increasing distance from span 38 in the direction of major axis 36.

In any event, one skilled in the art will readily appreciate that the wedge structure described herein allows tension in ligament 26 to be reduced by opening variable receiver 34 to permit distension of additional portions of span 40 into the tensile zone of ligament 26 located between receiver 30 and variable receiver 34.

In one form, the operation of system 10 for controlling tension in ligament 26 may be described as follows. During a surgical procedure, distensible ligament system 12, sensor 14 and drive system 16 with power supply 18 are implanted into the patient, and the surgical wounds are sutured or otherwise closed. Controller 20 may also be implanted during the same or a different surgical procedure, unless an external controller 20 is employed. Prior to or subsequent to the surgical procedure, controller 20 may be activated, e.g., turned on and booted.

During the surgical procedure, distensible ligament system may be initially set to have a variable opening 50 corresponding roughly to transverse dimension 74 of ligament 26. Transverse dimension 80 of node 66A is greater than transverse dimension 74, and hence, the length of ligament 26 as between receiver 30 and receiver 34 will not increase beyond the set point.

If subsequent movement of the patient or other conditions result in the tension in ligament 26 exceeding a predetermined limit, controller 20 directs the operations of drive unit 16 to reduce the tension. For example, sensor 14 transmits a signal to controller 20 indicative of tension in ligament 26. Controller 20 executes program instructions to compare tension with a first predetermined threshold. Upon the occurrence of the tension reaching or exceeding the first predetermined threshold, controller 20 generates a control signal to instruct drive unit 16 to open gate 46 a predetermined amount. The predetermined amount may be based on the degree to which the tension in ligament 26 exceeds the threshold.

In the present embodiment, the control signal is operative to direct drive unit 16 to rotate eccentric 48 by a predetermined amount from one position to another position, e.g., in rotational direction 58, which increases the size of opening 50, e.g., to a size corresponding roughly to transverse dimension 72 of ligament 26. Tension is released as a portion of span 40 is released into the now larger variable opening 50 until being stopped by the larger transverse dimension 78 of node 66B. An in vivo release of tension in ligament 26 is thus performed.

If subsequent movement of the patient or other conditions result in the tension in ligament 26 again exceeding a predetermined limit, controller 20 directs the operations of drive unit 16 to reduce the tension again. Sensor 14 transmits a signal to controller 20 indicative of tension in ligament 26. Controller 20 executes program instructions to compare tension with a second predetermined threshold. The second predetermined threshold may be the same as, greater than, or less than the first predetermined threshold. Upon the occurrence of the tension reaching or exceeding the second predetermined threshold, controller 20 generates another control signal to instruct drive unit 16 to open gate 46 another predetermined amount, which may be the same or different than the first predetermined amount. The predetermined amount may be based on the degree to which the tension in ligament 26 exceeds the threshold.

The control signal is operative to direct drive unit 16 to rotate eccentric 48 by a predetermined amount from one position to another position, e.g., in rotational direction 58, which increases the size of opening 50, e.g., to a size corresponding roughly to transverse dimension 70 of ligament 26. Tension is released as a second portion of span 40 is released into the even larger variable opening 50 until being stopped by the larger transverse dimension 76 of node 66C. A second in vivo release of tension in ligament 26 is thus performed.

Referring now to FIGS. 5A and 5B, another embodiment of a distensible ligament is illustrated. The embodiment of FIGS. 5A and 5B is a ligament 82 having a plurality of nodes 84, illustrated as nodes 84A, 84B and 84C. Extending from either side of nodes 84 are lineal extents 86, illustrated as lineal extents 86A, 86B and 86C and 86D. In the present embodiment, nodes 84 and lineal extents 86 may be constructed of the same material and fabricated similar to that described above with respect to ligament 26. They may also be the product of an assembly of elements which can occur during manufacture of each component, or thereafter. The material of nodes 84 and lineal extents 86 has a given elasticity/elongation and compressibility, which is known in the art, e.g., determined by the weave pattern, or structure, and/or the mechanical properties of the material used to make nodes 84 and lineal extents 86. Each node 84 includes an opening 88, illustrated as openings 88A, 88B and 88C. Openings 88 extend in a direction transverse to the length of ligament 82. Disposed within openings 88 are cushions 90, illustrated as cushions 90A, 9B and 90C. Nodes 84 with openings 88 and cushions 90 may have a different tensile elasticity than lineal extents 86. In embodiments of the present invention, the compressibility of nodes 84 may be different than the compressibility of lineal extents 86. In addition, openings 88 may be in the form of cavities and/or tunnels in ligament 82, which may be filled with cushion 90 material.

Cushions 90 may be made from a polymeric material, a hydrophilic material or a gel, and may have a different elasticity and/or compressibility than the material of nodes 84 and segments 86. Cushions 90 may be absorbable, and may be made from any compressible/deformable material suitable for implantation into a living being, such a human being.

Cushions 90 are transverse springs internal to ligament 82, and are used to control the overall distension of ligament 82 under tension. Other embodiments may employ other types of transverse spring elements that also provide a spring force to nodes 84 in a direction transverse or obliquely to the major axis of ligament 82, that is, transverse or in an oblique orientation to the axis extending along the length of ligament 82.

Ligament 82 may be coupled to bone tissue by anchors 92, e.g., having integral receivers, illustrated as anchors 92A and 92B. Anchors 92 with integral receivers may be similar to anchor 28 and receiver 30 of the previous embodiment. Anchor 92A may be secured to a first spinal vertebra or pelvic bone, and anchor 92B may be secured to a second spinal vertebra or pelvic bone, e.g., adjacent to the first spinal vertebra or pelvic structure.

Although the material of nodes 84 have the same elasticity as that of lineal segments 86, the inclusion of openings 88 in nodes 84 results in a geometry that lends additional elasticity/elongation to ligament 82, e.g., beyond that permitted by weave pattern and material properties. Thus, under tension, the nodes may collapse and flatten, and hence be elongated, resulting in a distension of ligament 82 greater than that which would be obtained in a ligament of the same material as nodes 84 and lineal extents 86, and the same length as ligament 82, but not having nodes 84 with openings 88 and cushions 90. The size and shape of openings 88 and the material of cushions 90 may be selected to yield a desirable elongation characteristic of ligament 82.

Embodiments of the present invention include a distensible ligament system which may include a ligament having a first span and a second span extending from the first span. The distensible ligament system may also include a first anchor including a first receiver. The first anchor may be structured for anchoring into a first bone tissue location. The first receiver may be structured to secure the first span to the first anchor. The distensible ligament system may also include a second anchor having a second receiver. The second anchor may be structured for anchoring into a second bone tissue location. The second receiver may be structured to secure the second span to the second anchor. The second receiver may be structured to perform an in vivo release of at least a portion of the second span.

In one refinement of the embodiment the second receiver includes a variable latch having a first position and a second position, and may include a drive unit structured to drive the variable latch from the first position to the second position to perform the in vivo release.

In another refinement of the embodiment the second receiver includes a gate having a variable opening. The gate may be structured to increase a size of the opening.

In another refinement of the embodiment the gate may include an eccentric having an axis of rotation. The rotation of the eccentric about the axis of rotation increases the size of the opening.

In another refinement of the embodiment the axis of rotation is substantially perpendicular to an axis through the major dimension of the ligament.

In another refinement of the embodiment the second span may include a segment having a ligament transverse dimension that increases with increasing distance from the first span.

In another refinement of the embodiment the second span may include a plurality of nodes of successively increasing ligament transverse dimension.

Another embodiment of the present invention is a system for controlling tension in a ligament which may include a sensor structured to provide a tension signal indicative of tension in the ligament. The system for controlling tension in a ligament may also include a variable receiver structured to perform an in vivo release of at least a portion of the ligament. The system for controlling tension in a ligament may also include a drive unit coupled to the variable receiver. The drive unit may be structured to receive a control signal, and in response thereto, to drive the variable receiver from a first position to a second position to perform the in vivo release. The system for controlling tension in a ligament may also include a controller communicatively coupled to the sensor and to the drive unit. The controller may be configured to execute program instructions to generate the control signal in response to the tension signal from the sensor.

In one refinement of the embodiment the sensor may be coupled to the ligament.

In another refinement of the embodiment the sensor may be positioned in the ligament.

In another refinement of the embodiment the controller may be communicatively coupled to the sensor via a wireless connection.

In another refinement of the embodiment the controller may be communicatively coupled to the drive unit via a wireless connection In another refinement of the embodiment the controller may be configured to execute program instructions to compare the tension with a first threshold, and transmit the control signal to the drive unit upon the occurrence of the tension reaching or exceeding the first threshold. The control signal may be operative to direct the drive unit to drive the variable receiver into the second position to perform the in vivo release, wherein the in vivo release releases a first portion of the ligament.

In another refinement of the embodiment the drive unit may also be structured to drive the variable receiver into a third position different from the second position based on the control signal. The controller may be configured to execute program instructions to compare the tension with a second threshold greater than the first threshold, and transmit the control signal to the drive unit upon the occurrence of the tension reaching or exceeding the second threshold. The control signal may be operative to direct the drive unit to drive the variable receiver into the third position to perform the in vivo release, and the in vivo release releases a second portion of the ligament.

Another embodiment of the present invention is a distensible ligament system which may include a ligament having a first span and a second span extending from the first span. The distensible ligament system may also include a means for anchoring the first span to a first bone tissue location, a means for anchoring the second span to a second bone tissue location, and a means for performing an in vivo release of at least a portion of the second span from the means for anchoring the second span.

One refinement of the embodiment may include a means for driving the means for performing the in vivo release.

Another refinement of the embodiment may include a means for determining tension in the ligament, and a means for controlling the means for performing based on an output of the means for determining.

Another embodiment of the present invention is a distensible ligament which may include a first extent having a first elasticity. The first extent may be structured for anchoring at a first bone tissue location. The distensible ligament may also include a node extending from the first extent. The node may have a second elasticity different from the first elasticity. The distensible ligament may also include a second extent extending from the node. The second extent may have the first elasticity, and the second extent may be structured for anchoring at a second bone tissue location.

In one refinement of the embodiment the node may include a transverse opening in the ligament.

Another refinement of the embodiment may include a transverse spring disposed in the transverse opening. The transverse spring may have a spring rate that determines the second elasticity.

In yet another refinement, the node has a different compressibility than the compressibility of the first extent.

In still another refinement, the node varies in width from the first extent.

While the invention has been described in connection with what is presently considered to be the most practical and preferred embodiment, it is to be understood that the invention is not to be limited to the disclosed embodiment(s), but on the contrary, is intended to cover various modifications and equivalent arrangements included within the spirit and scope of the appended claims, which scope is to be accorded the broadest interpretation so as to encompass all such modifications and equivalent structures as permitted under the law. Furthermore it should be understood that while the use of the word preferable, preferably, or preferred in the description above indicates that feature so described may be more desirable, it nonetheless may not be necessary and any embodiment lacking the same may be contemplated as within the scope of the invention, that scope being defined by the claims that follow. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

What is claimed is:

1. A distensible ligament system, comprising:
a ligament having a first span and a second span extending from said first span;
a first anchor including a first receiver, said first anchor being structured for anchoring into a first bone tissue location, wherein said first receiver is structured to secure said first span to said first anchor; and
a second anchor having a second receiver, said second anchor being structured for anchoring into a second bone tissue location, wherein said second receiver is structured to variably secure said second span to said second anchor such that a portion of said second span extends away from said first anchor and said second anchor, and wherein said second receiver is structured to perform an in vivo release of said portion of said second span when said second span is subjected to a tension exceeding a predetermined limit such that said portion of said second span is moved between said first and second anchors,
wherein said second span comprises an alternating plurality of nodes and a corresponding plurality of segments, said plurality of segments and said plurality of nodes increasing in transverse dimension with increasing distance from said first span.

2. The distensible ligament implant system of claim 1, wherein said second receiver is a variable latch having a first position and a second position, further comprising a drive unit structured to drive said variable latch from the first position to the second position to perform said in vivo release.

3. A distensible ligament system, comprising:
a ligament having a first span and a second span extending from said first span;
a first anchor including a first receiver, said first anchor being structured for anchoring into a first bone tissue location, wherein said first receiver is structured to secure said first span to said first anchor; and
a second anchor having a second receiver, said second anchor being structured for anchoring into a second bone tissue location, wherein said second receiver is structured to variably secure said second span to said second anchor such that a portion of said second span extends away from said first anchor and said second anchor, and wherein said second receiver is structured to perform an in vivo release of said portion of said second span when said second span is subjected to a tension exceeding a predetermined limit such that said portion of said second span is moved between said first and second anchors,
wherein said second receiver comprises a gate having a variable opening, said gate including an eccentric having an axis of rotation, wherein a rotation of said eccentric about said axis of rotation increases a size of said opening.

4. The distensible ligament implant system of claim 3, wherein said second receiver is a variable latch having a first position and a second position, further comprising a drive unit structured to drive said variable latch from the first position to the second position to perform said in vivo release.

5. The distensible ligament system of claim 3, wherein said axis of rotation is substantially perpendicular to an axis through the major dimension of said ligament.

6. The distensible ligament system of claim 3, wherein said second span includes a segment having a ligament transverse dimension that increases with increasing distance from said first span.

7. The distensible ligament system of claim 3, wherein said second span includes a plurality of nodes of successively increasing ligament transverse dimension.

* * * * *